(12) United States Patent
Zhang et al.

(10) Patent No.: US 12,268,560 B2
(45) Date of Patent: Apr. 8, 2025

(54) DEVICE AND METHOD FOR SUPPLYING POWER TO AN ULTRASOUND TRANSDUCER

(71) Applicants: UNIVERSITE PARIS-SACLAY, Gif-sur-Yvette (FR); CENTRE NATIONAL DE LA RECHERCHE SCIENTIFIQUE, Paris (FR)

(72) Inventors: Ming Zhang, Fontenay-sous-Bois (FR); Nicolas Llaser, Fontenay-sous-Bois (FR)

(73) Assignees: UNIVERSITE PARIS-SACLAY, Gif-sur-Yvette (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 132 days.

(21) Appl. No.: 18/006,378

(22) PCT Filed: Jul. 27, 2021

(86) PCT No.: PCT/EP2021/070955
§ 371 (c)(1),
(2) Date: Jan. 20, 2023

(87) PCT Pub. No.: WO2022/023316
PCT Pub. Date: Feb. 3, 2022

(65) Prior Publication Data
US 2023/0255603 A1    Aug. 17, 2023

(30) Foreign Application Priority Data
Jul. 30, 2020    (FR) .................................... 2008136

(51) Int. Cl.
*A61B 8/00*    (2006.01)
*A61N 7/00*    (2006.01)
(Continued)

(52) U.S. Cl.
CPC .............. *A61B 8/56* (2013.01); *A61N 7/00* (2013.01); *B06B 1/0215* (2013.01);
(Continued)

(58) Field of Classification Search
None
See application file for complete search history.

(56) References Cited

U.S. PATENT DOCUMENTS 9,692,445 B1 * 6/2017 Peterson .............. H03M 7/3042
10,613,205 B2 * 4/2020 Mortensen .......... G01S 15/8915
(Continued)

FOREIGN PATENT DOCUMENTS

CN    103167380 B    6/2013
CN    205426862 U    8/2016
(Continued)

OTHER PUBLICATIONS

International Search Report issued on Nov. 9, 2021 in corresponding International Patent Application No. PCT/EP2021/070955, 7 pages.
(Continued)

*Primary Examiner* — Colin T. Sakamoto
(74) *Attorney, Agent, or Firm* — Maier & Maier, PLLC

(57) ABSTRACT

A device for supplying an ultrasonic transducer including a power interface configured to provide an analog power signal, called supply signal, to the ultrasonic transducer, and further including a delta-sigma modulator configured to produce a delta-sigma modulator of a sinusoidal signal, called drive signal, and provide a digital signal, called control signal, to control said power interface. Also an ultrasonic device powered by such a supply device, an ultrasonic head including such ultrasonic devices and an ultrasonic system including such an ultrasonic head.

12 Claims, 4 Drawing Sheets

(51) Int. Cl.
    *B06B 1/02*    (2006.01)
    *H03M 3/00*    (2006.01)
(52) U.S. Cl.
    CPC ........... *B06B 2201/76* (2013.01); *H03M 3/30* (2013.01); *H03M 3/50* (2013.01)

(56) References Cited

U.S. PATENT DOCUMENTS

2014/0276065 A1* 9/2014 He .................. A61B 8/0891
                                                        600/445
2015/0109056 A1    4/2015 Lesso et al.
2019/0216426 A1    7/2019 Saroha et al.

FOREIGN PATENT DOCUMENTS

JP        H105218 A      1/1998
JP      2019530505 A    10/2019

OTHER PUBLICATIONS

Preliminary Search Report issued on Apr. 20, 2021 in corresponding French Patent Application No. 2008136, 18 pages.
Anonymous, "Delta-sigma modulation—Wikipedia", Mar. 25, 2020 (Mar. 25, 2020), Retrouvé de : URL:https://en.wikipedia.org/w/index.php?title=Delta-sigma_modulation&oldid=947299650, XP055793945.
Office Action issued on Sep. 3, 2024, in corresponding Japanese Application No. 2023-506185, 8 pages.

\* cited by examiner

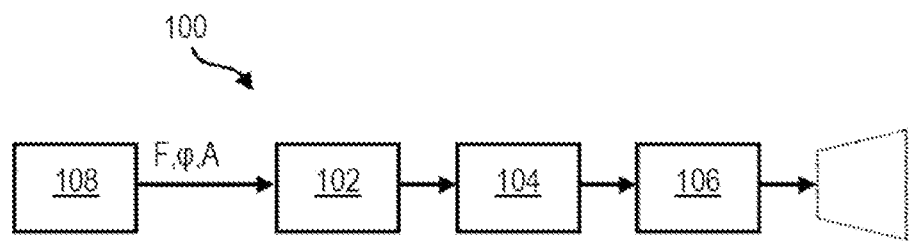
FIG. 1
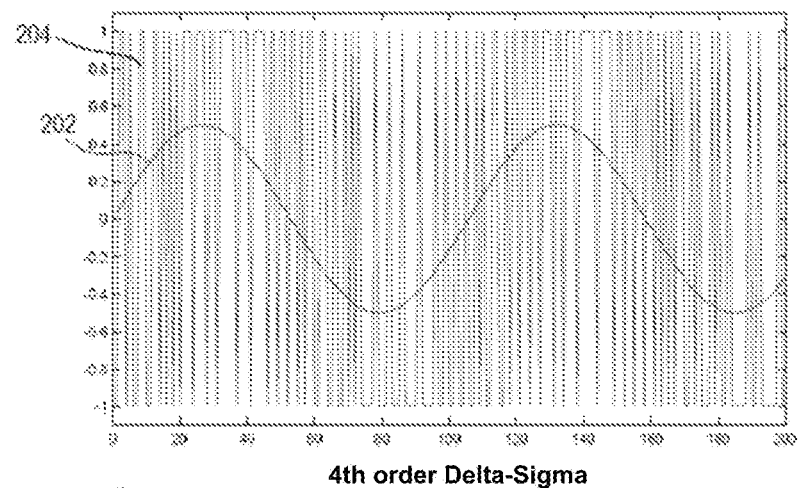
FIG. 2
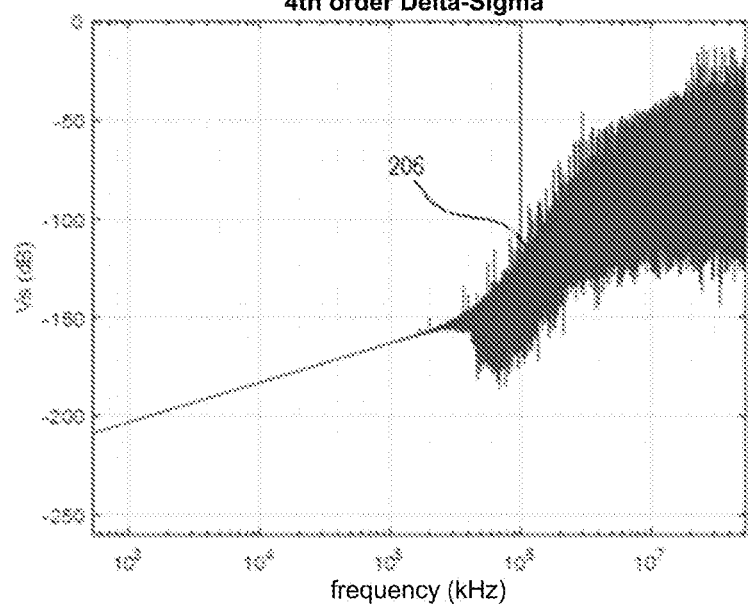

DEVICE AND METHOD FOR SUPPLYING POWER TO AN ULTRASOUND TRANSDUCER

The present invention relates to a device and a method for supplying an ultrasonic transducer. It also relates to an ultrasonic device comprising such a supply device, and an ultrasonic system comprising such an ultrasonic device.

FIELD

The field of the invention is the field of ultrasonic devices and in particular the field of supplying ultrasonic transducers, and in particular ultrasonic transducers for medical use.

BACKGROUND

Ultrasonic transducers are widely used in the medical field, in particular for medical imaging, for example for ultrasound examination, but also for medical therapy. To do this, the transducers are typically arranged in a matrix, also called an "ultrasonic head", in order to transmit focused and high-power ultrasounds in the area to be imaged or treated. Each ultrasonic transducer is supplied by a sinusoidal signal at a given frequency so as to generate an ultrasonic signal of said frequency.

Generally, the ultrasonic head comprises, for each ultrasonic transducer, an individual control chain. This latter makes it possible to modify, individually for each transducer, the amplitude of the ultrasonic signal transmitted by said transducer, but also its frequency and its phase. Thus, the characteristics of the ultrasonic wave transmitted by each transducer of the matrix can be modified.

However, the control chains known for ultrasonic transducers have degraded performance. Furthermore, the sinusoidal control signals provided by the known control chains are of poor quality such that the ultrasonic signal is degraded. Finally, the known control chains are generally bulky.

One aim of the present invention is to solve at least one of the above-mentioned shortcomings.

Another aim of the present invention is to propose a device for supplying an ultrasonic transducer that is more efficient in terms of performance.

Another aim of the present invention is to propose a device for supplying an ultrasonic transducer providing a better quality sinusoidal supply signal.

Another aim of the present invention is to propose a device for supplying an ultrasonic transducer that is less bulky.

SUMMARY

The invention makes it possible to achieve at least one of these aims with a device for supplying an ultrasonic transducer comprising a power interface configured to provide an analog power signal, called supply signal, to said ultrasonic transducer, characterized in that it further comprises a delta-sigma modulator configured to produce a delta-sigma modulation of a sinusoidal signal, called drive signal, and provide a digital signal, called control signal, to control said power interface.

In other words, the invention proposes to control the power interface supplying the sinusoidal supply signal to the ultrasonic transducer by a delta-sigma modulator through a delta-sigma modulated sinusoidal signal.

Thus, the device according to the invention makes it possible to supply the ultrasonic transducer with a better quality supply signal, and with improved performance relative to the known control chains. Indeed, the delta-sigma modulator makes it possible to provide a delta-sigma modulated sinusoidal signal for controlling a lower-cost and simple power interface. As a result, the supply signal of the transducer contains harmonics located in the high frequencies outside of its bandwidth.

Furthermore, the delta-sigma modulator can be made in the form of a digital component so that the supply device is less cumbersome, compared to currently known analog control chains. In addition, the use of a delta-sigma modulator makes it possible to avoid the use of a filter dedicated to harmonic elimination, which further reduces the size of the supply device according to the invention.

The reduction in the size of the supply device according to the invention makes it possible to reduce the size of the ultrasonic head compared to current ultrasonic heads, or to increase the number of transducers of the ultrasonic head with a constant size.

The delta-sigma modulator may be of any order.

For example, the delta-sigma modulator may be a $4^{th}$ order modulator.

According to one embodiment, the delta-sigma modulator may comprise a single-bit output quantizer such that the control signal is modulated over one bit.

In this case, the power interface may, for example, be a half H-bridge controlled by the delta-sigma modulated control signal.

According to one embodiment, the delta-sigma modulator may comprise a multi-bit output quantizer such that the control signal is modulated over several bits.

In this case, the power interface can, for example, be a group of switches, each connected to a particular fixed voltage, controlled by the delta-sigma modulated control signal. In particular, when the control signal is over two bits, four switches and the voltage source thereof are necessary. Generally, the power interface is adapted to the number of bits of the control signal.

Advantageously, the drive signal can be a digital sinusoidal signal, i.e. a sinusoidal signal in digital form, in other words, a sinusoidal signal represented in digital form traditionally encoded as "n" bits, complement to base 2.

In this case, the supply device according to the invention may further comprise a digital generator configured to generate said drive signal, according to any combination of at least one of the following parameters:
 a frequency of said drive signal,
 an amplitude of said drive signal,
 a phase of said drive signal.

Such a generator can be an electronic chip, or any other digital component programmed to generate, in digital form, an analog signal based on input data representing the at least one of the listed parameters.

According to one advantageous feature, the supply device according to the invention may comprise a digital control interface providing any combination of at least one of the following parameters:
 a data item relating to a frequency of said drive signal,
 a data item relating to an amplitude of said drive signal,
 a data item relating to a phase of said drive signal.

Such a digital control interface may be, or may comprise, a digital communication interface intended to receive data representing at least one of the listed parameters, from an external control device.

Alternatively, such a digital control interface may be, or may comprise, computational intelligence making it possible to deduce at least one of the listed parameters as a function of other data provided thereto, such as for example power data, a focal length, etc.

The digital control interface may be provided to perform wireless communication with the external control device.

Alternatively, or in addition, the digital control interface may be provided to perform wired communication, with the external control device, via a digital communication bus.

The supply device according to the invention may be integrated, partly or entirely, into at least one digital component, such as an electronic chip or a processor, in particular programmable.

In particular, all the elements of the supply device according to the invention, except the power interface, may be integrated into a digital component, such as an electronic chip or a processor, in particular programmable.

According to one advantageous feature, the delta-sigma modulator may be integrated into a digital component, such as an electronic chip or a processor, in particular programmable, with the digital signal generator, and/or the digital control interface.

According to another aspect of the invention, an ultrasonic device is proposed comprising:
at least one ultrasonic transducer, and
a supply device according to the invention for supplying said at least one ultrasonic transducer.

The ultrasonic transducer may be a transducer of any type.

In particular, the ultrasonic transducer may be an ultrasonic transducer used for medical applications, in particular for medical imaging such as ultrasound examination, or medical treatment such as ecotherapy, or even for aesthetic applications.

According to another aspect of the present invention, an ultrasonic head is proposed comprising several ultrasonic devices according to the invention, in parallel.

In the ultrasonic head according to the invention, each ultrasonic transducer is associated with a supply device dedicated thereto such that each ultrasonic transducer can be individually controlled. Thus, the characteristics of the ultrasonic wave generated by each ultrasonic transducer of the ultrasonic head according to the invention can be modified individually.

In particular, the amplitude, frequency and phase of the ultrasonic wave transmitted by each ultrasonic transducer of the ultrasonic head can be modified for each ultrasonic transducer individually.

The ultrasonic head according to the invention can be used for medical imaging, in particular for ultrasound imaging.

Alternatively, or in addition, the ultrasonic head according to the invention can be used for medical therapy.

Alternatively, or in addition, the ultrasonic head according to the invention can be used for aesthetic treatment.

According to another aspect of the present invention, an ultrasonic system is proposed comprising:
an ultrasonic head according to the invention, and
at least one digital control device for the ultrasonic devices of said ultrasonic head.

According to one embodiment, the ultrasonic system according to the invention may comprise, for at least one, and in particular each, ultrasonic device of the ultrasonic head, an individual digital control device dedicated to said ultrasonic device.

In this case, each ultrasonic device of the ultrasonic head receives the data concerning the ultrasonic wave to be generated from the digital control device dedicated thereto.

According to another embodiment, the ultrasonic system according to the invention may comprise a digital control device common to several, and in particular to all, ultrasonic devices.

Thus, each ultrasonic device receives the data concerning the ultrasonic wave to be generated from said common digital control device.

The common digital control device may be connected to the ultrasonic devices by a wired digital communication bus.

Alternatively, said common digital control device may be connected to said ultrasonic devices by a wireless connection, for example of the Wi-Fi or Bluetooth type, and more generally a wireless radiofrequency connection.

Alternatively, said common digital control device can be connected to said ultrasonic devices by an optical connection.

In all cases, the data defining the ultrasonic wave to be generated by each ultrasonic device may be transmitted to the digital control interface of said ultrasonic device.

The system according to the invention may be a medical imaging system.

The system according to the invention may be an ultrasound imaging system. In this case, the system may comprise, in a known manner, means for processing ultrasonic waves to generate at least one ultrasound image.

The system according to the invention may be a medical therapy system.

In particular, the system according to the invention may be an ecotherapy system.

The system according to the invention may be an aesthetic treatment system.

According to another aspect of the invention, a use of the system according to the invention is proposed for medical imaging.

According to another aspect of the invention, a use of the system according to the invention, for the aesthetic treatment of at least one zone of the body of a human being or animal, is proposed.

According to another aspect of the invention, a method is proposed for supplying an ultrasonic transducer with an analog power signal, called supply signal, characterized in that it comprises the following steps:
delta-sigma modulation of a sinusoidal signal, called drive signal, to provide a signal, called control signal;
controlling a power interface with said delta-sigma modulated control signal, to provide said supply signal.

Of course, the method according to the invention can comprise, in terms of method, any combination of at least one feature described above, and which are not repeated herein for the sake of brevity.

BRIEF DESCRIPTION OF THE FIGURES

Other benefits and features shall become evident upon examining the detailed description of an entirely non-limiting embodiment, and from the enclosed drawings in which:

FIG. 1 is a schematic depiction of a non-limiting exemplary embodiment of a supply device for an ultrasonic transducer;

FIG. 2 is a schematic depiction of a non-limiting example of examples of signals in the device of FIG. 1;

DETAILED DESCRIPTION

Figure 3:
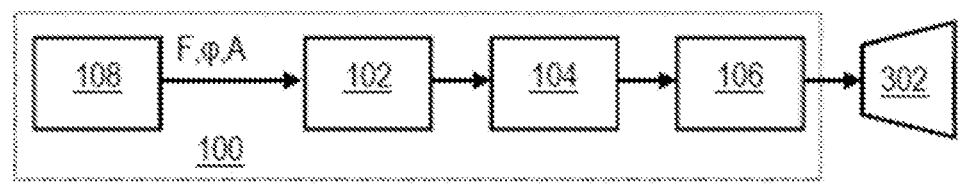
FIG. 3 is a schematic representation of a non-limiting exemplary embodiment of an ultrasonic device according to the invention.

It is clearly understood that the embodiments that will be described hereinafter are by no means limiting. In particular, it is possible to imagine variants of the invention that comprise only a selection of the features disclosed hereinafter in isolation from the other features disclosed, if this selection of features is sufficient to confer a technical benefit or to differentiate the invention with respect to the prior state of the art. This selection comprises at least one preferably functional feature that lacks structural details, or only has a portion of the structural details if that portion is only sufficient to confer a technical benefit or to differentiate the invention with respect to the prior state of the art.

In the figures the same reference has been used for the elements that are common to several figures.

FIG. 1 is a schematic depiction of a non-limiting exemplary embodiment of a supply device according to the invention.

The device 100, shown in FIG. 1, is provided to supply an ultrasonic transducer, for example, in an ultrasonic transducer of an ultrasonic head for medical use.

The supply device 100 comprises a digital sinusoidal signal generator 102 that generates a digital sinusoidal signal, i.e. a sinusoidal signal represented in digital form, and called the drive signal hereinafter. This digital generator 102 can be any digital electronic component programmed or designed to deliver, in digital form, the sinusoidal drive signal, as a function of the parameters relating to the sinusoidal signal to be generated. For example, the parameters entered into the digital generator 102 may comprise:

the frequency F, and/or
the phase φ, and/or
the amplitude A of the sinusoidal signal to be generated.

The digital generator 102 therefore provides a digital signal representing a sinusoidal signal, and called drive signal. The phase and frequency of the drive signal correspond respectively to the frequency and to the phase of the ultrasonic wave to be generated.

Of course, the use of such a digital generator in the device according to the invention is optional and the drive signal may be provided by an external device.

The device 100 further comprises a delta-sigma converter 104, also called a DS converter hereinafter. The DS converter 104 receives the drive signal and performs a delta-sigma conversion of said drive signal to provide a signal, called control signal. In other words, the control signal provided by the DS converter 104 is a delta-sigma representation of the drive signal that itself is a digital signal representing a sinusoidal signal.

The DS converter 104 may be of any order.

The DS converter 104 may comprise a single-bit or multi-bit output quantizer.

The supply device 100 comprises a power interface 106 designed to deliver a supply signal supplying an ultrasonic transducer. The supply signal delivered by the power interface 106 is a high voltage sinusoidal signal, for example between 10 V and 100 V, and with a power of a few watts. The ultrasonic transducer converts this supply signal into an ultrasonic wave whose frequency is equal to the frequency of the supply signal.

The power interface 106 is controlled by the control signal supplied by the DS converter 104. In other words, the control signal 106 adjusts the operation of the power interface 106 so that the latter supplies the supply signal. The power interface 106 may be a half H-bridge or an H-bridge or else a group of switches, controlled by the control signal supplied by the DS converter. In this case, the power interface 106 comprises, in a known manner, a DC voltage source, or receives a DC voltage from an external source. The control signal supplied by the DS converter 104 controls the operation of the power interface 106 that provides, at the output, a DS modulated sinusoidal supply voltage.

In the example shown, the supply device 100 comprises a control interface 108, upstream of the digital generator 102. The control interface is arranged to provide the digital generator 102 with the features of the sinusoidal signal to be generated, namely the frequency F, and/or the phase φ, and/or the amplitude A.

The control interface 108 may be provided to receive at least one of these features from an external device with which it is in communication.

Alternatively, the control interface 108 can be programmed to deduce at least one of these features based on other data, such as a focal length of the ultrasonic wave to be generated or a power value of the ultrasonic wave to be generated, for example.

Of course, the use of such a control interface is optional and the features of the sinusoidal signal may be communicated directly to the digital generator 102.

Each of the modules 102-108 may be produced digitally. In particular, at least the DS converter 104 is produced digitally.

In FIG. 1, each of the modules 102-108 is represented individually. Of course, at least two of these modules may be integrated into a single digital component, such as a chip or a processor. In particular, the DS converter 104 and the digital generator 102 may be integrated into the same digital component.

FIG. 2 is a schematic depiction of non-limiting examples of signals in the device of FIG. 1.

Thus, in FIG. 2:

the signal 202 corresponds to the curve that represents the digital signal supplied by the generator 102 to the DS modulator;

the signal 204 corresponds to the delta-sigma modulated control signal produced by the DS converter 104, which, in this example, has a single-bit output, by virtue of the signal 202 and the signal 206 corresponds to the spectrum of the signal produced by the interface 106 that supplies the transducer. This signal is, in this example, produced by a DS modulator of the $4^{th}$ single-bit order.

FIG. 3 is a schematic depiction of a non-limiting exemplary embodiment of an ultrasonic device according to the invention.

The ultrasonic device 300 depicted in FIG. 3 comprises an ultrasonic transducer 302 powered by a supply device according to the invention, and in particular the supply device 100 of FIG. 1.

Figure 4:
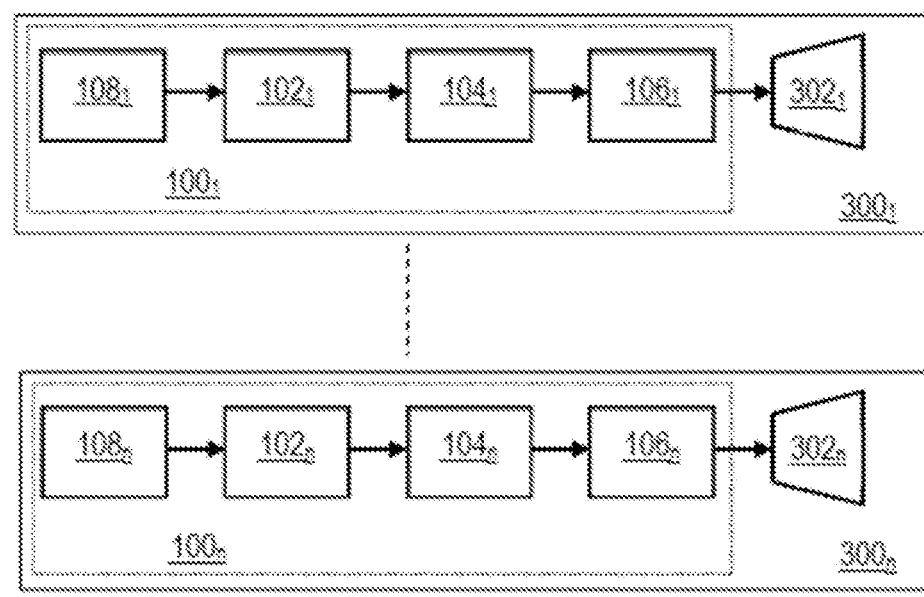
FIG. 4 is a schematic depiction of a non-limiting exemplary embodiment of an ultrasonic head according to the invention.

FIG. 4 is a schematic depiction of a non-limiting exemplary embodiment of an ultrasonic head according to the invention.

The ultrasonic head 400 of FIG. 4 comprises "n" ultrasonic devices $300_1$-$300_n$ arranged in parallel and forming a matrix.

At least two of the ultrasonic devices $300_1$-$300_n$ may be identical or different.

Each ultrasonic device $300_i$ may be identical to the ultrasonic device 300 of FIG. 3 and comprises all the elements of the device 300 with the same references supplemented by "i" as a suffix.

Figure 5:
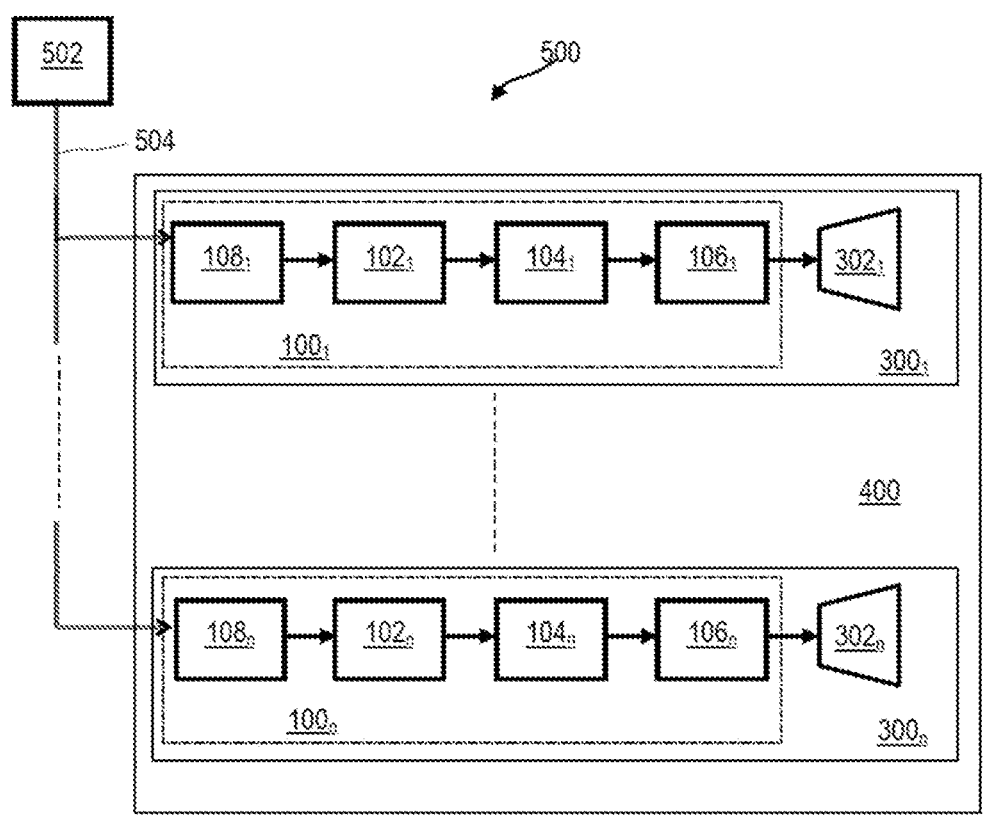
FIG. 5 is a schematic depiction of a non-limiting exemplary embodiment of an ultrasonic system according to the invention.

FIG. 5 is a schematic depiction of a non-limiting exemplary of an ultrasound system according to the invention.

The ultrasound system 500 of FIG. 5 comprises an ultrasonic head according to the invention, such as for example the ultrasonic head 400 of FIG. 4.

The ultrasonic system 500 further comprises a control device 502, such as a computer or a tablet, and more generally any computer device, connected to each ultrasonic device $300_i$ of the ultrasonic head 400, and in particular to the control interface $108_i$ of said ultrasonic device.

In the example depicted, the control device 502 is connected to each control interface $108_i$ via a communication bus 504 that is digital and wired 504. Alternatively, each control interface $108_i$ may be in communication with the control device 502 through a wireless link.

The control device 502 makes it possible to control each ultrasonic device $300_i$ individually and independently of the other ultrasonic devices $300_i$ to change the frequency, phase and/or amplitude of the ultrasonic wave emitted by each ultrasonic device $300_i$. This makes it possible to adjust, in a simple, dynamic and reactive manner, the amplitude, frequency and phase of each ultrasonic wave emitted by each ultrasonic device $300_i$. Consequently, it is possible to adjust in a simple, flexible and reactive manner the focal point, and the amplitude of the ultrasonic waves emitted by the ultrasonic devices $300_1$-$300_n$.

Thus, when the invention is implemented in a medical imaging device, it is possible to track the moving members.

Figure 6:
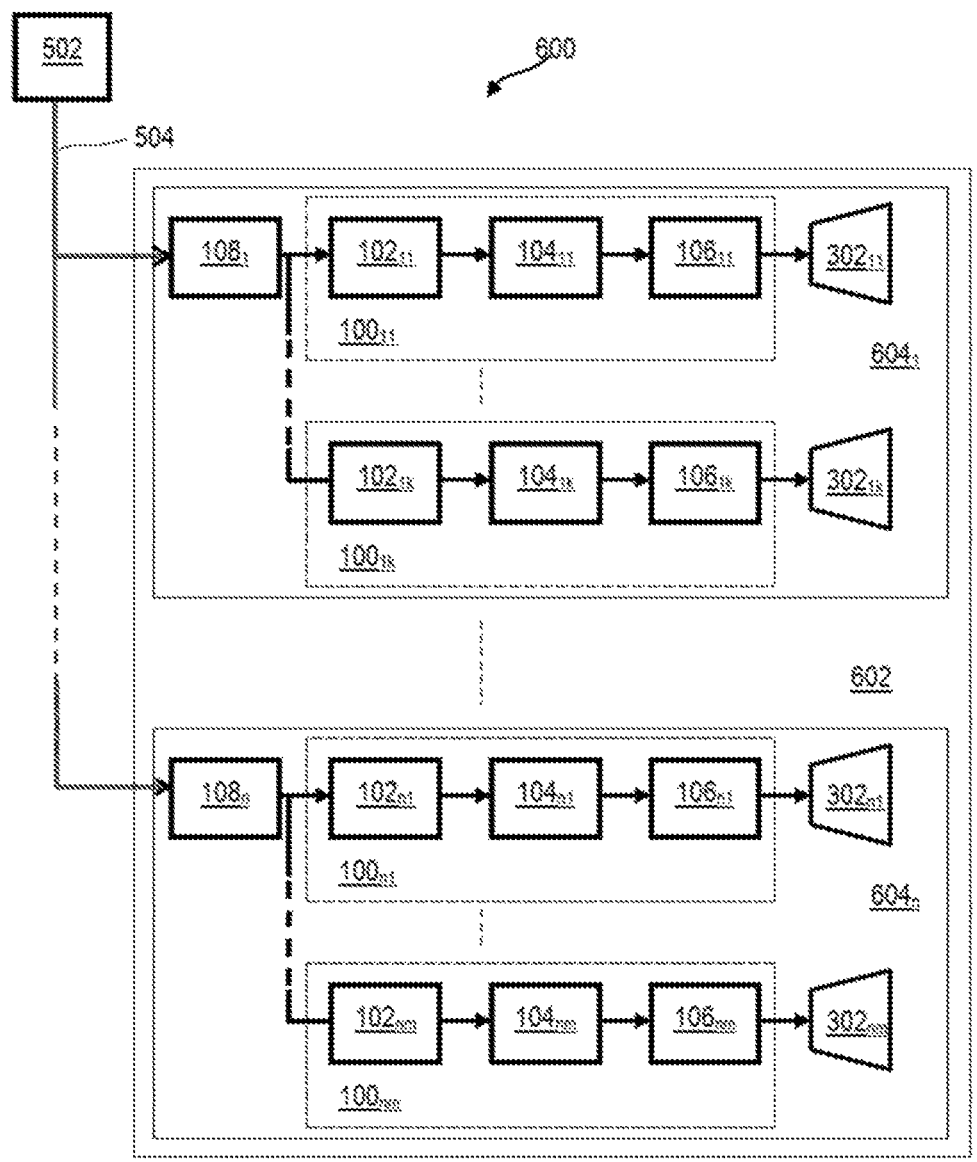
FIG. 6 is a schematic depiction of another non-limiting exemplary embodiment of an ultrasonic system according to the invention.

FIG. 6 is a schematic depiction of another non-limiting exemplary embodiment of an ultrasonic system according to the invention.

FIG. 6 illustrates a variant of FIG. 5, wherein the system 600, shown in FIG. 6, has a head 602 composed of a plurality of 'n' composite ultrasonic devices $604_1$ to $604_n$. Within each of these composite ultrasonic devices $604_i$, a same common interface $108_i$ controls a plurality of supply devices that each supply one and only one transducer. For example, within the ultrasonic device $604_1$, a same common interface $108_1$ controls a plurality of 'k' supply devices $100_{11}$ to $100_{1k}$, which each supply one and only one transducer $302_{11}$ to $302_{1k}$. In the same way, the block $604_n$ comprises a single digital interface $108_n$ that directly drives the 'm' supply devices $100_{n1}$ to $100_{nm}$ of the transducers respectively $302_{n1}$ to $302_{nm}$.

This makes it possible to produce a digital interface block $108_1$ to $108_n$, each of which is capable of directly driving a group of several transducers of the matrix.

The matrix then consists of a multitude of transducers, which are associated in 'n' groups comprising an identical or different number of transducers. In general, the number of transducers in a given group is small, for example in a number from 2 to 16.

Thus, it is for example possible to improve compactness and the number of components at the level of the digital interfaces within the head. It is also possible to industrially produce a compact and standard sub-assembly including a digital interface and several transducers; which standard sub-assembly may be used in different configurations to produce different types of heads.

Of course, the invention is not limited to the examples detailed above.

The invention claimed is:

1. A device for supplying an ultrasonic transducer comprising a power interface configured to provide an analog power signal, called supply signal, to said ultrasonic transducer; wherein said device further comprises a delta-sigma modulator configured to produce a delta-sigma modulation of a sinusoidal signal, called drive signal, and provide a digital signal, called control signal, to control said power interface.

2. The device according to claim 1, wherein the delta-sigma modulator comprises a single-bit output quantizer such that the control signal is modulated over one bit.

3. The device according to claim 1, wherein the delta-sigma modulator comprises a multi-bit output quantizer such that the control signal is modulated over several bits.

4. The device according to claim 1, wherein the drive signal is a digital sinusoidal signal, said device further comprising a digital generator configured to:
receive as input data any combination of at least one parameter selected from the group consisting of:
a frequency of said drive signal,
an amplitude of said drive signal, and
a phase of said drive signal; and
generate said drive signal from said at least one parameter.

5. The device according to claim 1, wherein said device further comprises a digital control interface providing at least one parameter selected from the group consisting of:
a frequency of said drive signal,
an amplitude of said drive signal, and
a phase of said drive signal.

6. The device according to claim 1, wherein said device is integrated, partly or entirely, into at least one digital component.

7. An ultrasonic device comprising:
at least one ultrasonic transducer, and
a supply device, according to claim 1, for supplying said at least one ultrasonic transducer.

8. An ultrasonic head comprising several ultrasonic devices according to claim 7, in parallel.

9. An ultrasonic system, comprising:
an ultrasonic head according to claim 8, and
at least one digital control device for the ultrasonic devices of said ultrasonic head.

10. The system according to claim 9, wherein said ultrasonic system is a medical imaging, or therapy, system.

11. The system according to claim 10, wherein said ultrasonic system is a medical imaging system.

12. A method for supplying an ultrasonic transducer with an analog power signal, called supply signal, said method comprising the following steps:
delta-sigma modulation of a sinusoidal signal, called drive signal, to provide a signal, called control signal; and
controlling a power interface with said delta-sigma modulated control signal, to provide said supply signal.

* * * * *